United States Patent [19]
Tamburrino et al.

[11] Patent Number: 5,253,638
[45] Date of Patent: Oct. 19, 1993

[54] RIGHT-ANGLE DETACHABLE VARIABLE-POSITION REFLECTOR ASSEMBLY

[75] Inventors: Richard A. Tamburrino, Auburn; Alan S. Knieriem, Syracuse, both of N.Y.

[73] Assignee: Welch Allyn, Inc., Skaneateles Falls, N.Y.

[21] Appl. No.: 857,620

[22] Filed: Mar. 25, 1992

[51] Int. Cl.$^5$ .............................................. A61B 1/06
[52] U.S. Cl. ...................................... 128/6; 359/367; 403/107
[58] Field of Search ................. 128/21, 6, 4; 359/367, 359/831, 833; 403/104, 106, 107, 111, 108, 83, 335; 285/82, 84, 184

[56] References Cited

U.S. PATENT DOCUMENTS

| | | | |
|---|---|---|---|
| 3,749,088 | 7/1973 | Kohlmann | 403/107 X |
| 4,727,859 | 3/1988 | Lia | . |
| 5,122,900 | 6/1992 | Tamburrino et al. | 359/367 |

*Primary Examiner*—Richard J. Apley
*Assistant Examiner*—Karen A. Jalbert
*Attorney, Agent, or Firm*—Wall and Roehrig

[57] ABSTRACT

A side-looking reflector attachment has a helical thread on the borescope or endoscope the reflector attachment can be rotated to any angular position by drawing the housing distally to move a retaining pin in the housing out of engagement with a recess in a threaded retaining ring. The housing and the mirror can be rotated to align the mirror with the probe imager. Then, the housing is released and the retaining pin then enters a recess at a new position. This arrangement renders the side looking attachment interchangeable from one probe to another.

6 Claims, 2 Drawing Sheets

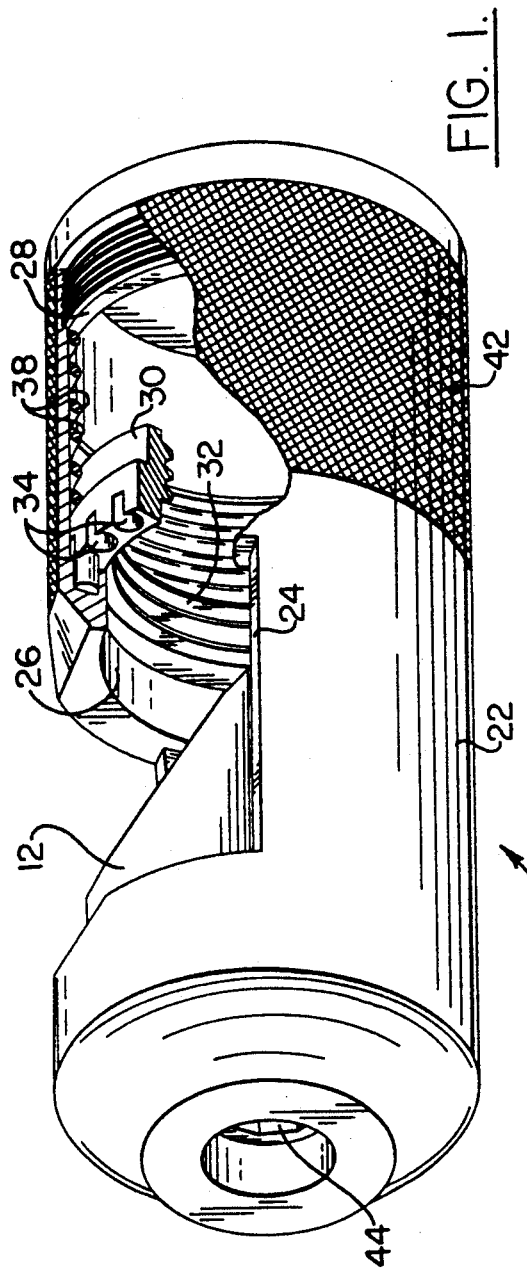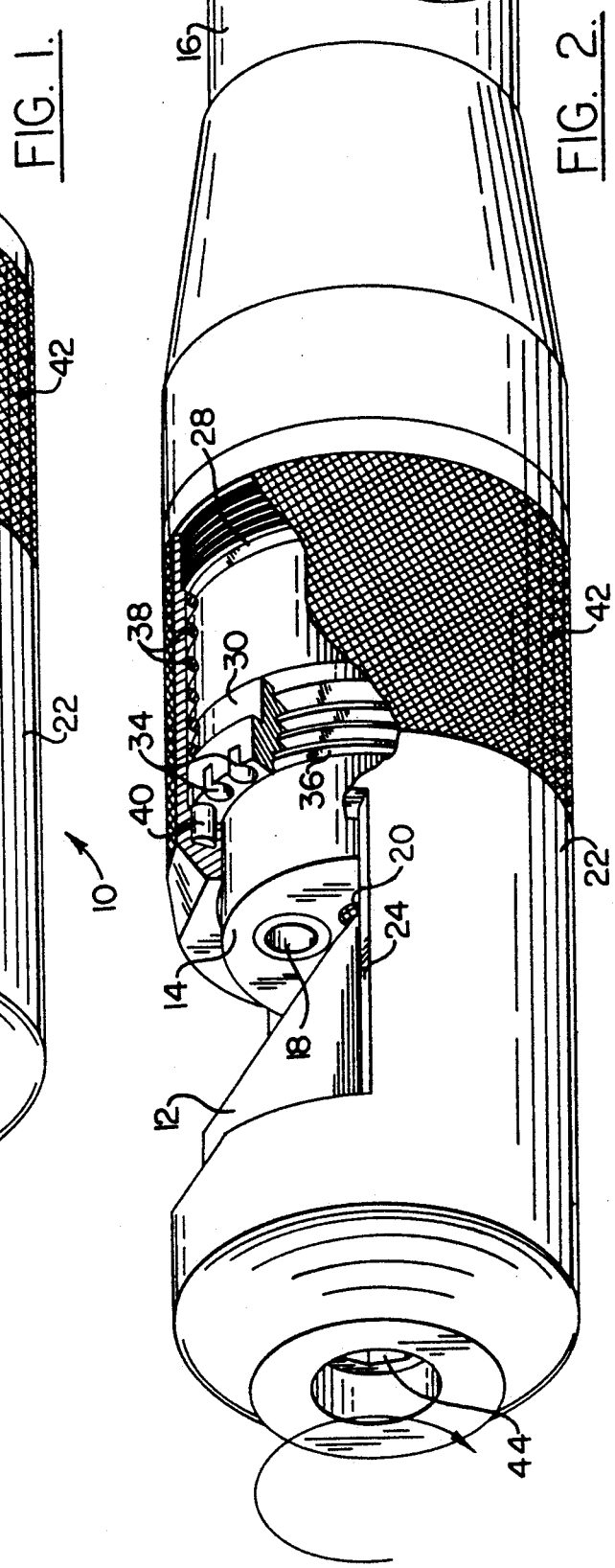

RIGHT-ANGLE DETACHABLE VARIABLE-POSITION REFLECTOR ASSEMBLY

BACKGROUND OF THE INVENTION

This invention relates to borescopes and endoscopes, which are long, flexible instruments which carry a viewing device at the end of an elongated insertion tube. Borescopes are intended for inspection of concealed machine parts and the like, for example, inspection of vanes of a turbine or jet engine without disassembly thereof.

The present invention is more particularly concerned with a detachable right angle reflector assembly that is demountably attached onto the viewing head on the distal end of the borescope insertion tube.

For many borescope applications forward viewing is required, but for other applications side viewing is needed. That is, it is sometimes necessary to view a hidden or obstructed target from a direction that is more or less radial with respect to the axis of the borescope. To permit both forward and side viewing with the same instrument, a detachable right angle optics assembly can be employed.

One detachable right angle prism assembly is shown and described in U.S. Pat. No. 4,727,859 to Raymond A. Lia. In that arrangement a housing is coupled by a bayonet fitting onto the viewing head, and includes a right angle prism that changes the viewing direction of the image sensor from axial (straight ahead) to radial (sideward). Because the assembly uses a bayonet coupling, alignment of the image sensor and the mirror or prisms is easily achieved, and the right angle viewer can be interchanged among several borescopes of the same type.

In many borescopes, particularly those which may have large, oversize illumination fiber bundles and/or wide viewing angles, the large outside diameter of the borescope distal tip presents a design constraint. In large-diameter borescopes, the use of a threaded coupling is required, rather than a bayonet mechanism. However, when the right angle viewer is attached by helical threads to the viewing head of the probe, each viewer and probe have to be made as a matched pair, and interchangeability is difficult or impossible to accomplish, since the alignment of the mirror or prism to the image sensor is determined by the amount of thread engagement. Matching thread engagements for a probe and a sideview mirror assembly are impractical to manufacture, because of variations in thread cutting and polish dimensions on the probe head.

OBJECTS AND SUMMARY OF THE INVENTION

It is a general object of this invention to provide a sideview mirror or prism assembly that avoids the drawbacks of the prior art, and permits mounting onto a borescope or similar probe by means of helical threads.

It is another object of this invention to provide a sideview mirror or prism arrangement in which the orientation of the reflector relative to the image sensor of the probe is variable to permit alignment of the mirror or prism with the probe.

It is a further object to provide a side viewing reflector attachment that is interchangeable from one probe to another.

According to one aspect of this invention the right angle detachable mirror or prism assembly has a generally tubular housing or cap that overfits the distal end of the head of the probe. A mirror (or equivalent reflector means) is mounted within the housing along the optic axis of the image sensor to redirect the viewing angle to the side, through a window provided on the side of the housing. A threaded mounting ring is disposed in the housing proximally of the mirror, and has female threads that engage and mount onto male helical threads on the probe head. A helical compression spring is positioned between the ring and retaining structure on the proximal end of the housing. The spring acts to urge the ring distally within the housing, i.e., to urge the housing proximally with respect to the probe head on which the ring is mounted. The ring is provided with a series of detents, for example bores or recesses in the distal face, and these detents are spaced around the ring at regular intervals. A cooperating member, e.g. a proximally facing pin, is mounted on the inside wall of the housing and engages one of the recesses to interlock the housing and the ring against rotation. The pin is held in the recess by the compressive force of the spring. The right angle viewing assembly is attached onto the probe head by engaging the threaded ring and the probe threads and rotating the assembly until the ring is tightly engaged on the probe head.

After the assembly is mounted on the head, the operator can grasp the mirror housing and pull it distally, away from the head. This causes the spring to compress and pulls the pin out of engagement with the recess in the ring. Then the operator can rotate the housing to reposition the mirror or prism relative to the image sensor and any associated light guides to obtain an optimal viewing angle.

After this, the operator releases the housing, and the pin enters engagement with another recess to lock the mirror into the new orientation.

Of course, other detent means besides a pin and recesses on the ring could be used. In one embodiment there are thirty recesses on the ring, spaced at about twelve degrees. This permits accurate alignment within about six degrees.

The above and many other objects, features, and advantages of this invention will be more fully understood from the ensuing description of a preferred embodiment, which should be considered in connection with the accompanying Drawing.

BRIEF DESCRIPTION OF THE DRAWING

FIG. 1 is a perspective view, partly cut away, of a right angle mirror assembly according to one preferred embodiment of the invention.

FIG. 2 shows the assembly of FIG. 1 installed on the viewing head of a borescope or similar probe.

DETAILED DESCRIPTION OF THE PREFERRED EMBODIMENT

Figure 3:
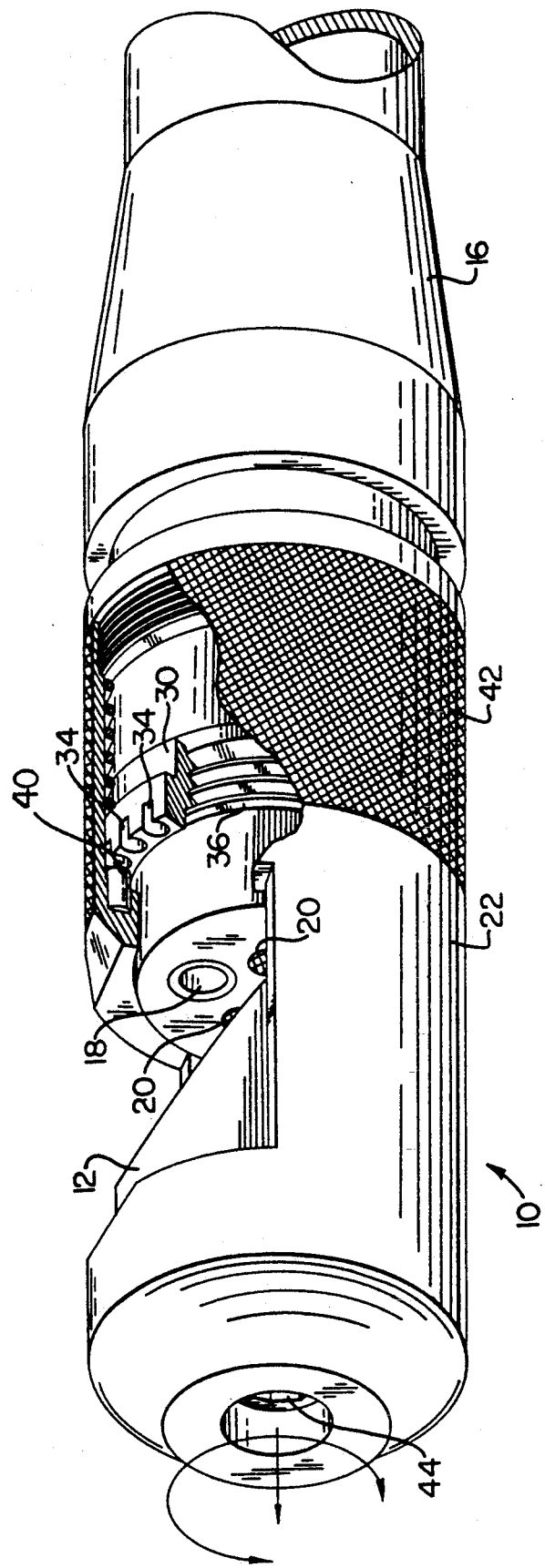
FIG. 3 shows the assembly of FIG. 1 with the housing pulled forward to permit alignment of the right angle mirror with the imaging and illumination optics of the probe.

With reference to the Drawing, and initially to FIGS. 1 and 2, the right angle viewing attachment 10 according to one preferred embodiment has a mirror 12 oriented at 45° from the axis of a viewing head 14 that is positioned at a distal tip of a borescope insertion tube 16. The viewing head 14 has an imaging device 18, which can be either a fiber optic imager or a video imager, as well as fiber optic bundles 20 for illumination. As shown in FIG. 1, the attachment 10 has a tubular housing 22 with a cutout or window 24 through which the mirror 12 redirects the viewing direction of the associated imaging device 18. The housing 22 has a distal shoulder 26 positioned just proximal of the window 24 and a proximal shoulder 28 at the proximal end of the housing 22. In this case the shoulder is in the form of a threaded fitting. A fitting ring 30 is disposed within the housing 22 against the distal shoulder 26. The ring is provided with female interior threads 32 and with cylindrical recesses 34 on a distal surface of the ring 30. These recesses are evenly distributed around the ring 30 and in this particular embodiment there are thirty recess 34 spaced at 12 degree intervals.

The female threads 32 of the ring 30 couple with male helical threads 36 that are provided on a cylindrical outer surface of the viewing head 14.

A helical compression spring 38 is situated against an inner wall of the housing 22 and is compressed between the ring 30 and the proximal shoulder 28. The spring 38 fits within an annular gap between the housing 22 and the outer cylindrical wall of the borescope viewing head 14.

A retaining pin 40, which is axially oriented, is implanted in the shoulder 26. The pin 40 enters one of the recesses 34 and thus holds the ring 30 against rotation with respect to the housing 22.

Also shown in FIG. 1 is a knurled surface 42 on the proximal portion of the housing 22, and a hexagonal receptacle 44 at the distal end of the housing 22. This receptacle 44 accepts a hex wrench to facilitate tightening of the mirror 12 into housing 22. The hex wrench can also be employed for removal of the mirror.

Because of difficulties or impracticalities in forming of identical threads 36 in a series of borescopes the position of the mirror 12, which is affixed in the housing 22, will not always align properly with the imaging device 18 or with the illumination fiber optic bundles 20. The right angle attachment 10 is installed by rotating the housing 22 until the threads 32 are sufficiently tightened onto the threads 36 on the viewing head 14. At this stage, the pin 40 holds the housing 22 and the mirror 12 against rotation with respect to the ring 30. To align the mirror 12 with the imaging device 18, the operator can grasp the housing 22 and pull it distally, i.e., away from the head 14 to the position as shown in FIG. 3. Pulling the housing 22 distally compresses the spring 38 and moves the pin 40 out of engagement from the associated recess 34. This permits rotation of the housing 22 relative to the ring 30. Now the operator rotates the housing 22 to position the angular orientation of the mirror 12 relative to the imaging device 18 and the fiber optic bundles or light guides 20. This obtains an optimum viewing angle. Then the operator releases the housing 22, and the pin 40 engages into another recess 34 at the new position. Thereupon, the borescope is ready for use for side viewing.

While a single retaining pin 40 is shown here, more than one pin could be employed. Also, rather than the pin-and-recess configuration, a ball type detent could be employed, as could a crown gear arrangement or any of numerous other releasably interlocking means for releasably securing the ring 30 with respect to the housing 22.

Moreover, while a mirror 12 is used here as the reflector, in other possible embodiments one or more prisms could be used.

It should be understood that this invention is not limited to the precise embodiments depicted here, but rather, many modifications and variations would present themselves to those of skill in the art without departing from the scope and spirit of this invention, as defined in the appended claims.

What is claimed is:

1. Right-angle detachable variable-position prism or mirror assembly for a borescope of the type that includes an insertion tube with a viewing head at its distal end, the head having a distally-facing image sensor oriented parallel to a longitudinal axis of the borescope viewing head, and a helical male thread on a peripheral wall of said head; the prism or mirror assembly comprising:

a generally tubular housing adapted to overfit the distal end of said head;

a reflector mounted in said housing along an optical axis of the image sensor for reflecting to the latter light that enters a window on one side of the housing;

a mounting ring disposed within said housing proximally of said reflector and having a female thread adapted for mounting onto the helical thread of said borescope head;

biasing means positioned in said housing between said ring and a proximal end of said housing and urging the housing proximally with respect to said borescope head on which said ring is adapted to be mounted; and a plurality of detent means spaced around a distal face of said ring and cooperating with at least one engaging means affixed to the interior of said housing; wherein said engaging means normally interlocks with one of said detent means on said ring to hold the housing and reflector against rotation relative to said ring and said borescope head, but said engaging means is freed from said detent means by pulling said housing distally after which the housing and reflector can be rotated to a new rotational position relative to said head and said ring, and upon release of said housing said biasing means urges said engaging means to interlock with another of said detent means to hold said housing and said reflector at said new rotational position.

2. The assembly of claim 1 wherein said biasing means includes a helical compression spring disposed between said mounting ring and an annular shoulder at the proximal end of the tubular housing.

3. The assembly of claim 1 wherein said detent means includes a plurality of recesses formed at spaced intervals around the ring.

4. The assembly of claim 3 wherein said engaging means includes a retaining pin mounted to said housing and engaging with one of said recesses.

5. The assembly of claim 3 wherein said detent means include at least thirty said recesses spaced at even intervals.

6. The assembly of claim 1 wherein a proximal portion of the housing has a knurled outer surface.

* * * * *